United States Patent [19]
Johansson et al.

[11] Patent Number: 5,274,244
[45] Date of Patent: Dec. 28, 1993

[54] METHOD AND APPARATUS FOR DETECTING BARK AND FOR DETERMINING THE DEGREE OF BARKING ON WOOD AND CHIPS

[75] Inventors: Lennart Johansson, Sörberge; Leif Ringström, Stockholm, both of Sweden

[73] Assignee: STFI, Stockholm, Sweden

[21] Appl. No.: 855,650

[22] PCT Filed: Nov. 9, 1990

[86] PCT No.: PCT/SE90/00728
§ 371 Date: May 18, 1992
§ 102(e) Date: May 18, 1992

[87] PCT Pub. No.: WO91/07653
PCT Pub. Date: May 30, 1991

[30] Foreign Application Priority Data
Nov. 14, 1989 [SE] Sweden .............................. 8903821

[51] Int. Cl.$^5$ .............................................. G01N 21/88
[52] U.S. Cl. ........................................ 250/563; 250/572
[58] Field of Search ............. 250/571, 572, 562, 563; 356/429, 430, 431, 237, 445, 369; 209/517, 518, 521

[56] References Cited

U.S. PATENT DOCUMENTS

| | | | |
|---|---|---|---|
| 3,976,384 | 8/1976 | Matthews et al. | 356/200 |
| 4,245,913 | 1/1981 | Sarlos | 356/431 |
| 4,266,675 | 5/1981 | Barwise et al. | 209/540 |
| 4,482,250 | 11/1984 | Hirvonen et al. | 356/369 |
| 4,606,645 | 8/1986 | Mathews et al. | 356/445 |

FOREIGN PATENT DOCUMENTS 64301 7/1983 Finland .

*Primary Examiner*—David C. Nelms
*Assistant Examiner*—K. Shami
*Attorney, Agent, or Firm*—Burns, Doane, Swecker & Mathis

[57] ABSTRACT

The present invention relates to a method and to an apparatus for detecting the presence of bark and for determining the barking degree of wood or chips. Accordingly, the apparatus includes a light source (12) which directs a concentrated light beam (14) onto the measurement object (16), for instance a log which is moved continuously in a transport chute (20). The shape and/or size of the light image obtained on the log (16) at the point (18) on which the light beam (14) impinges on the log is detected with the aid of a camera (10), preferably a CCD-camera. The shape and/or size of the light image is mutually different for wood and bark. The detection values obtained by the CCD-camera (10) are evaluated in a processing means.

17 Claims, 5 Drawing Sheets

METHOD AND APPARATUS FOR DETECTING BARK AND FOR DETERMINING THE DEGREE OF BARKING ON WOOD AND CHIPS

The present invention relates to a method and to apparatus for continuously indicating the presence of bark on such material as logs and chips, and/or for determining the extent to which such material has been barked.

In the manufacture of wood-based paper pulp, it is extremely important, both with respect to product quality and production economy, to ensure that bark has been removed from the wood with sufficient thoroughness. Depending on the final product desired, wood which is delivered to the refinery or to the digester may be allowed to have a maximum bark percentage of 0.3-2%. The separation of bark from such material should not, however, be undertaken too strenuously, since this will result in the removal of wood together with the bark. This loss of good wood can have a very noticeable effect on the production economy of the mill concerned. Thus, in the manufacture of paper pulp, it is extremely important to debark the wood or the chips to an optimum degree. This optimum barking degree also varies from product to product and between the various manufacturing processes applied.

In order to achieve this optimum barking degree, it is not only necessary to adapt the barking process with respect to the product and the process concerned, but also to the nature of the wood starting material. Mutually different treatment times and treatment intensities are required when debarking different types wood, e.g. wood which has been felled or logged at different times of the year, and also with respect to the length of time the wood has been stored, the dryness of the wood, and whether or not the wood is frozen or thawed. The wood used in a pulp mill is seldom of uniform quality, due to availability and variations throughout the year, these variations often being unknown, and, consequently, it is often impossible to achieve an optimum degree of debarking. It is therefore desirable to be able to determine the barking result continuously and in a rational manner, so that corrections can be made in the bark separating process.

One significant drawback in this respect is that hitherto there has been no objective method for determining the degree of barking of wood or chips rapidly. The only quick method used hitherto involves inspecting the wood or chips visually, with subjective assessment of the extent to which the wood or chips has been barked. This method, however, is not reliable and continuous inspection of the wood material is also very expensive and extremely tiring for the persons involved. The objective methods applied hitherto have been manual. One method is to separate bark from the wood or the chips and then dry and weigh the two constituents individually, such as to enable a measurement of the degree of barking to be obtained. Alternatively, a measurement is taken of the total area of bark remaining on a log and this measurement compared with the total mantle area of the log. Since these objective methods are highly work intensive and expensive, they are only applied on singular occasions, for instance when testing new installations or plants in order to ensure that guarantees are fulfilled, or in the case of special process studies.

SE-400 381 teaches a method and apparatus for the optical detection of faults in sawn or planed timber.

The apparatus includes, for instance, a light source and a light detector, each of which is located on a respective side of an opaque screen having a thickness of about 2 mm. The light detector sends signals to a comparator which produces an output signal when light that falls on the detector produces an electric signal which exceeds a threshhold value. A fault, for instance in the form of twigs, blue-stained wood, and certain types of decay, is indicated in dependence on the intensity of the light reflected. This apparatus can only be used on sawn or planed timber, where the surface is so smooth and regular as to enable the opaque screen to be connected to the surface of the timber, and where product requirements include relatively well-defined requirements on the optical properties of the timber surface with respect to colour, brightness, etc. The contour extensions of logs or chips intended for pulp manufacture vary rapidly and extensively. Even though means could be provided which will enable the screen to follow the surface of the wood material, the colour and brightness of wood and bark would vary considerably, and consequently this known method would not be sufficiently precise. The method cannot therefore be used for detecting the extent to which logs or chips have been barked.

SE-404 964 teaches an apparatus for detecting radiation from an object for the purpose of establishing surface deviations or faults. This known apparatus is intended for sorting timber, for instance green board, dried board and planks, and deviations in the form of bark residues are detected through the intensity of the light reflected. For the same reasons as those given above, this known apparatus cannot be used for detecting the extent to which logs or chips have been barked, since the origin of the wood and the bark, their condition and the geometrical attitude of the surface, e.g. its inclination, etc. vary considerably.

These problems are solved by the inventive method and the inventive apparatus, which have the characterizing features set forth in the respective characterizing clauses of claim 1 and claim 10 respectively. The inventive method and apparatus enable the degree of barking on wood or chips to be detected and determined continuously, therewith enabling the separation of bark to be adjusted to an optimum barking degree on the wood or the chips concerned.

One difficulty with detecting and determining the barking degree of wood or chips is that of distinguishing between bark and wood. Normally, it is expected that wood is light in colour and bark is dark. This is not always the case, however, since wood can also be dark or coloured. Furthermore, wood can become dark or coloured as a result of storage, decay and like processes. A large part of the wood used in the manufacture of pulp has been stored over different lengths of time. The inner bark of spruce, for instance, and also a number of other wood types, can also be light in colour, as can also the bark of birch. Consequently, it is not sufficient to utilize solely the brightness or colour of the wood material when determining whether the object seen is bark or wood.

The method and the apparatus according to the present invention utilize differences in the optical properties of the bark and the wood, such as the light scattering, light reflection and light absorption properties, for the purpose of determining the barking degree of wood or chips. Because of its long fibres, wood is a more orientated material than bark. When concentrated light impinges on the surface of wood, the light will propagate within the wood material to a far greater extent in the longitudinal direction of the fibres and the wood than in the transverse direction thereof. There is obtained an elongated light image. This effect is generally greater in the case of wood than in the case of bark. Thus, when light falls on wood and bark respectively, there is obtained a bark light image and a wood light image of mutually different size and shape.

The invention will now be described in more detail with reference to an exemplifying embodiment thereof and also with reference to the accompanying drawings, in which FIGS. 1a and 1b illustrate respectively the light images obtained with wood and with bark;

Figure 1A:
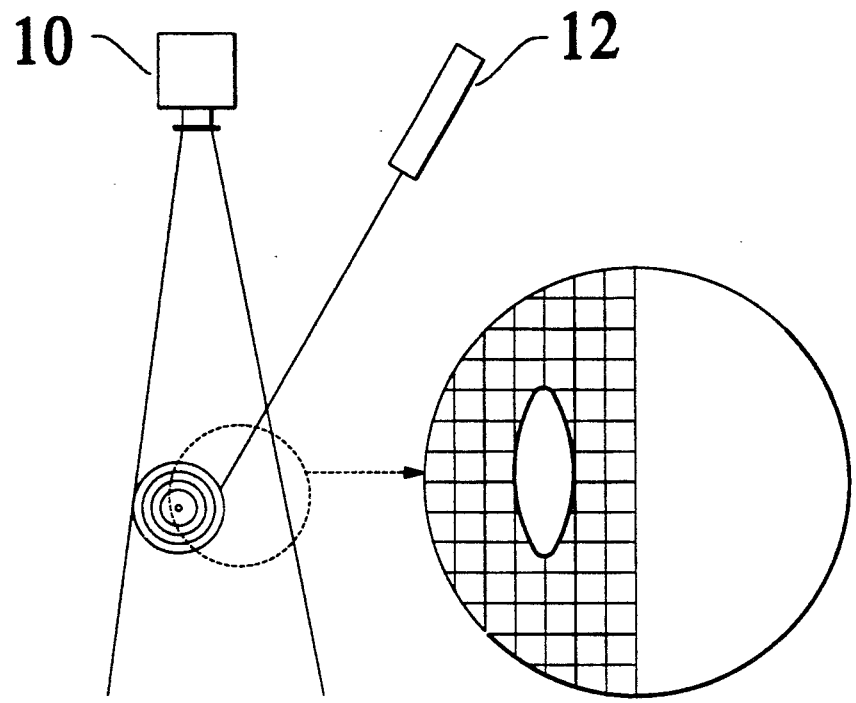
Figure 1B:
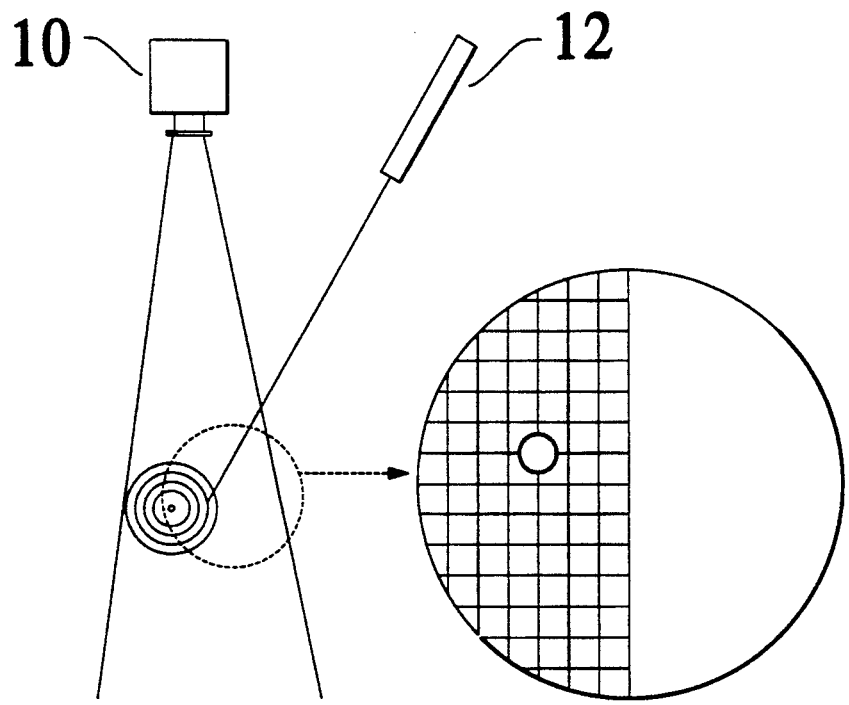

When practicing the inventive method and using the inventive apparatus, at least one concentrated light beam is directed onto material in the form of wood or chips, therewith to obtain a light image of the material. The light images thus obtained will have different shapes and sizes, depending on whether the light beam impinges on wood or bark. When the light beam, for instance a laser beam, impinges on a clean wood surface, the light is spread in the wood fibres in a manner which produces an oval light image. See in this respect FIG. 1a. When the laser beam, on the other hand, impinges on a bark surface, the light is spread to such a small extent that the light image obtained will have the form of a spot of small diameter. See in this respect FIG. 1b. The reference numerals 10 and 12 used in FIGS. 1a and 1b designate respectively a detecting device and a laser. The light images shown in FIGS. 1a and 1b are illustrated in the same way as they are detected by the detecting device 10.

Figure 3:
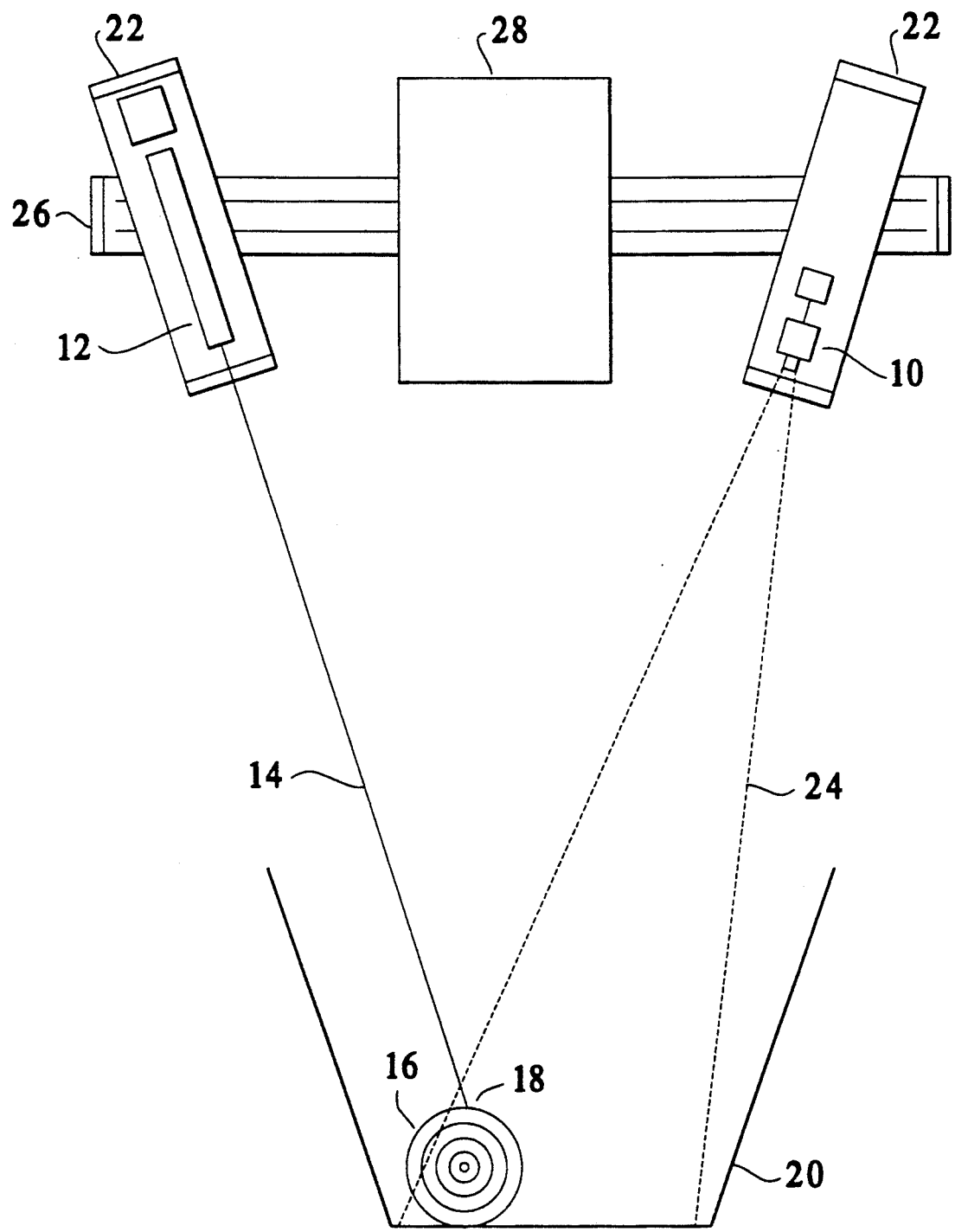
FIG. 3 is a side view, partly in cross-section, of one embodiment of apparatus constructed in accordance with the invention.

FIG. 3 illustrates an embodiment of the inventive apparatus. The apparatus includes a laser 12 which functions to direct a concentrated light beam, in the form of a laser beam 14, onto a measurement object 16 in the form of a log. The object 16 may also be a wood chip. At the point 18 at which the laser beam 14 impinges on the log 16, there is obtained a light image whose shape and size depends on whether the light beam 14 has impinged on wood or bark. (Compare FIGS. 1a and 1b). The shape and size of the light image is detected by a detector device 10, in the form of a camera, preferably a CCD-camera having a field of view 24. The use of a camera enables the light image detected by the camera to be determined in two dimensions, i.e. in size and shape. In the case of simpler applications, it is sufficient to determine the area of the light image by counting the number of picture elements of the camera which detects a light level which is greater than a threshhold value. Both the laser 12 and the camera 10 are housed in a respective protective housing 22, so as to protect the laser and camera from the environment prevailing in wood-based pulp manufacturing mills. Each of the housings 22 is mounted on a respective rotatable plate (not shown), so that the angle between the laser 12 and the camera 10 can be adjusted. In turn, the rotatable plates can be displaced along a mounting bar 26, so as to enable the distance between the laser 12 and the camera 10 to be changed. The reference numeral 28 designates an electronic system which includes process means for evaluating the signal received from the camera. The measurement object 16 (illustrated in the form of a log 16) is moved continuously past the measuring area on a transport chute 20 (shown in cross-section) to a cutter (where the logs are cut into chip form). The degree of barking is then determined by the processing device in accordance with the relationship:

$$\frac{\text{Number of Measurements Small Light Images}}{\text{Total Number of Measurements}}$$

The surfacewise notation of the barking degree of the logs can be converted to volume or a weightwise notation when the diameters of the logs are known, or is measured, while taking into account the thickness of the bark and the density of the wood and the bark.

Figure 4:
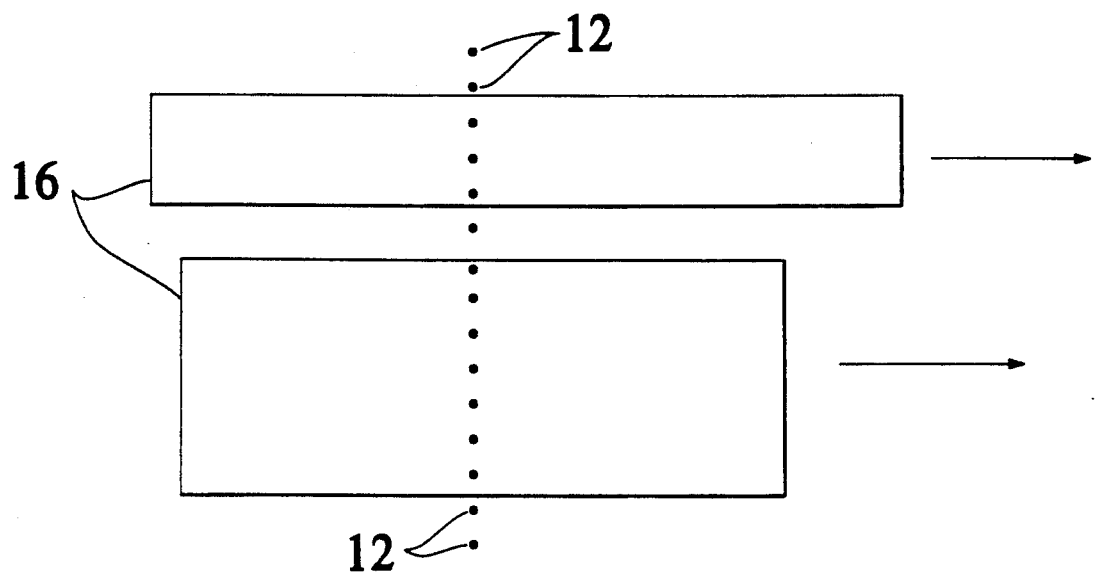
FIG. 4 illustrates the principle of an alternative embodiment of the inventive apparatus.

FIG. 4 illustrates the principle of another embodiment of the inventive apparatus, which comprises a plurality of lasers 12 which are arranged on a line extending perpendicularly to the direction of movement of the measurement object 16. In other respects, the apparatus comprises the same components as those included in the apparatus illustrated in FIG. 3. The lasers 12 need not necessarily be disposed along a line, but can be arranged in any other suitable manner which will enable the material to be illuminated in different positions transversely to the direction of movement.

Figure 5:
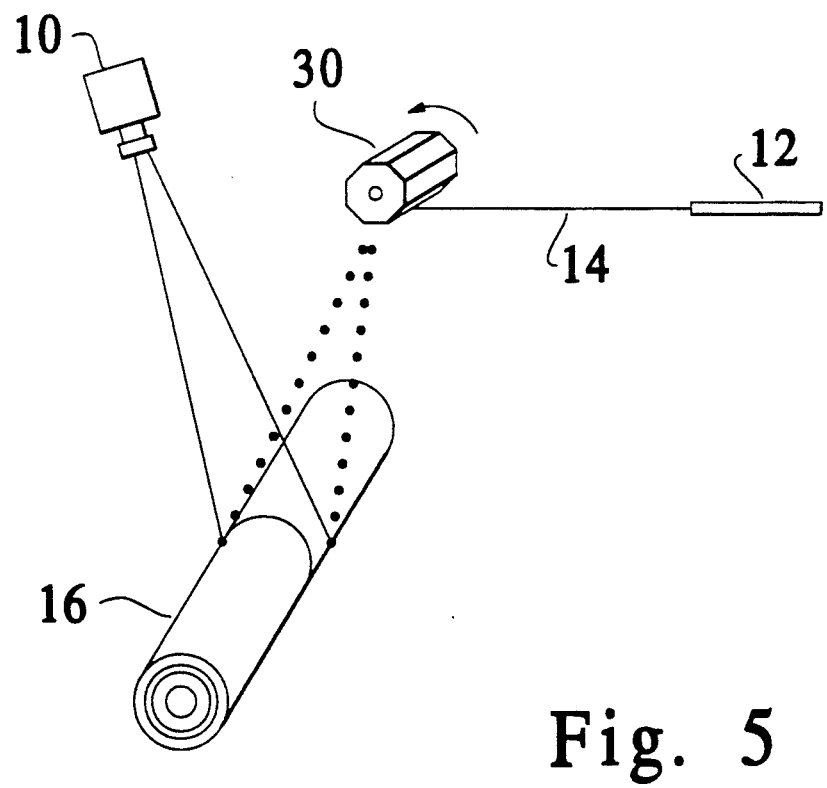
FIG. 5 illustrates the principle of a further alternative embodiment of the inventive apparatus.

FIG. 5 illustrates the principle of a further embodiment of the inventive apparatus, which comprises a laser 12 and a rotating prism 30 which sweeps the laser beam 14 obtained from the laser 12 over the measurement object 16. A camera 10 functions to detect the two-dimensional extension of the light image produced on the measurement object 16 by the laser beam 14. The advantage with this principle is that a large number of measurements can be made on each measurement object and it is also possible to determine the diameter of said object in accordance with known methods. Alternatively, there can be used a lens arrangement such that the light beam, obtained for instance from a laser, will provide on the measurement object a linear light image, wherewith the width of the line can be determined on intermittent occasions with the aid of a camera, in order to determine whether bark or wood is illuminated.

Figure 2:
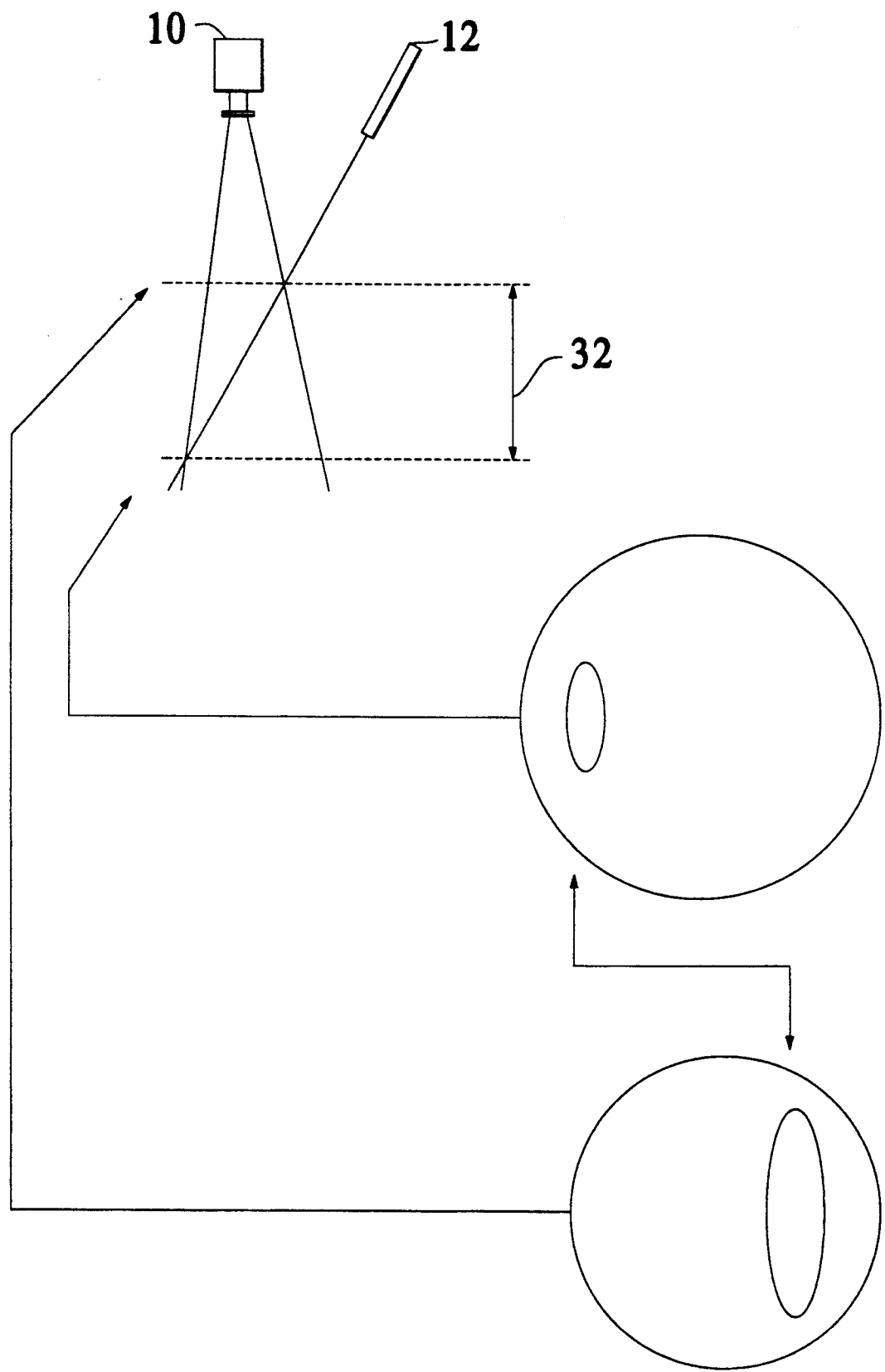
FIG. 2 illustrates the principle applied for adjusting the size of the detected light image upon deviation from a nominal focusing distance.

Because of the inability of the camera to focus at all ranges, it is possible that the light images will appear to have different sizes. Compare FIG. 2. Whether or not this will cause a disturbance will depend on such features as the distance to the measurement object, the depth of the measurement area and the performance of the optics. In such case, the actual extensions of the light image can be determined prior to determining the degree of barking. The actual or prevailing extensions of the light image are determined by compensating for the deviation d from the focal distance of the camera, in accordance with the relationship: actual extension=- measured extension−f(d). In the case of standard accuracy requirements, the following approximation can be applied: f(d)=k·d².

In the embodiment illustrated in FIG. 3, the light source and detector are arranged so that the deviation d, for instance, can be calculated from the location of the detected light image in the camera viewing field. Compare FIG. 2. The reference numeral 32 designates the measuring depth of the apparatus. In this case, the focal distance of the camera lies in the proximity of the bottom end of the measuring depth. The measuring depth 32 is determined by the angle between the camera 10 and the laser 12.

Figure 6:
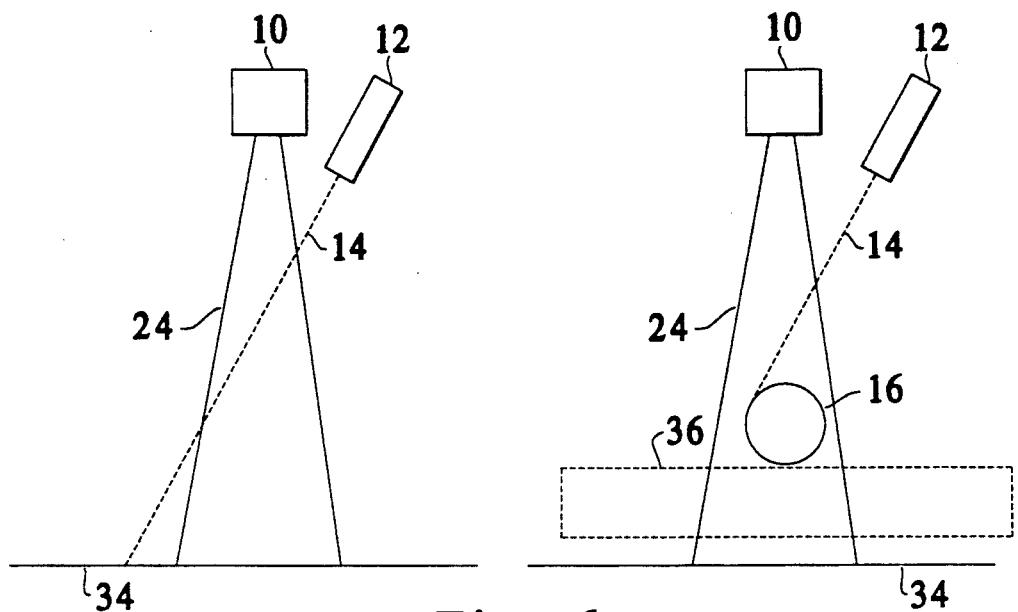
FIG. 6 illustrates a method of distinguishing bark and wood-material from background.

The manner in which the method and apparatus operate is also dependent on the ability to distinguish the bark and wood material from background material. One method of achieving this distinction is illustrated in FIG. 6, in which the background 34 is located at a distance from the transport rollers 36 on which the measurement object 16 is transported in the case of the illustrated embodiment. In the FIG. 6 embodiment, the laser beam 14 falls at an angle such that a light point on the background 34 will lie externally of the area that can be observed by the camera 10.

Figure 7:
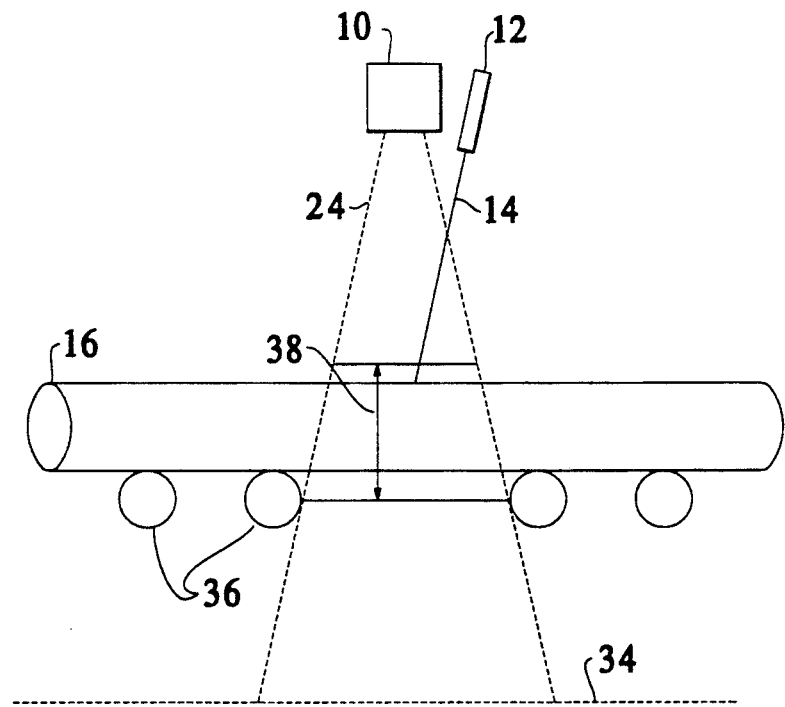
FIG. 7 illustrates a further method of distinguishing bark and wood-material from background.

FIG. 7 illustrates an alternative method of distinguishing the bark and wood material from the background. In this case, the camera 10 and the laser 12 are so positioned that only a small field-of-depth area 38, which is focused on the bark and wood material, is utilized during the detection process.

Another method of solving the aforesaid problem is to permit the background to have optical properties different to those of bark and wood material.

We claim:

1. A method for continuously establishing the presence of bark on a material such as logs and wood chips, and/or for determining the barking degree of said material with the aid of at least one concentrated light beam directed onto the surface of the material and moving relatively to said material, said method including the steps of:
    detecting the size and/or shape of the light image obtained on said surface with the aid of the light beam, said size and/or shape constituting criteria relating to the constituents of the material, whereby an elongated light image is obtained when the light beam impinges on a wood surface that is substantially free from bark depending on the spreading of the light in the wood fibers and a light image in the form of a light spot is obtained when the light beam impinges on a bark surface since the light is spread to a smaller extent in bark than on a wood surface that is substantially free from bark, and
    evaluating the detected values.

2. A method according to claim 1, further comprising the step of employing linear illumination and detecting the with of the light image on the material intermittently.

3. A method according to claim 1, further comprising the steps of sweeping the light beam, e.g. in the form of a laser beam, over the material and detecting the two-dimensional extension of the light image obtained on the material.

4. A method according to claim 4, further comprising the steps of directing a plurality of the light beams onto the surface of the material, and detecting the two-dimensional extensions of the light images obtained on the surface of said material.

5. A method according to claims 1-4, further comprising the steps of determining the actual extension of the light image by adjusting the extension of the detected light image in dependence on the distance between a detecting device, used to effect said detection, and the material.

6. A method according to claim 5, further comprising the steps of determining the actual extension of the light image with the aid of the relationship:

*Actual Extension=Detcted Extension−f(d),* where, for instance, the following approximation can be used:

*f(d)=k·d2,* wherein d is a deviation from the focus distance of the camera.

7. A method according to claim 1, further comprising the step of illuminating the material at an angle such as to make it impossible to observe a light image on the backround of the marerial.

8. A method according to claim 1, wherein said method being further characterized in that the material and the backround have essentially different optical properties.

9. A method according to claim 1, further characterized by using light in the wavelength range of 600–1300 nm.

10. Apparatus for continuously establishing the presence of bark on a material such as logs or wood chips, and/or determining the barking degree of the material, said apparatus comprising:
    means for producing a concentrated light beam on the surface of the material;
    a detecting device which functions to detect the size and/or the shape of a light image obtained on said surface with the aid of the light beam, said shape and size constituting criteria related to the constituents of the material, whereby an elongated light image is obtained when the light beam impinges on a wood surface that is substantially free from bark depending on the spreading of the light in the wood fibers and a light image with the form of a light spot is obtained when the light beam impinges on a bark surface since the light is spread to a smaller extent in bark than on a wood surface that is substantially free from bark, and
    processing means which coact with the detecting device for evaluating the detected values.

11. Apparatus according to claim 10, wherein the means for producing the concentrated light beam is a laser.

12. Apparatus according to claim 11, wherein light in the wavelength range of 600–1300 nm is used.

13. Apparatus according to claim 10, wherein the detection device is a camera, e.g. a CCD-camera.

14. Apparatus according to claim 10, further comprising a rotating prism which functions to sweep the concentrated light beam over the material, wherein the extension of the light image produced on the material is determined with the aid of the detection device.

15. Apparatus according to claim 10, further comprising a linear optic, which influences the concentrated light beam in a manner such that the light image produced on the material will have the form of a line, wherein the width of said line is determined intermittently with the aid of the detection device.

16. Apparatus according to claim 10, characterized by one or more light sources which produce a plurality of concentrated light images on the material (16), wherein the detection device functions to determine the extension of the light images.

17. Apparatus according to claim 10, wherein the processing means functions to determine the actual extension of the light image in dependence on the distance between the detection device and the material in accordance with the relationship:

*Actual Extension = Detected Extension − f(d),* where, for instance, the following approximation can be used:

$$f(d) = k \cdot d2,$$

wherein d is the deviation from the focus distance of the camera.

* * * * *